United States Patent [19]

Hamprecht et al.

[11] Patent Number: 4,585,472
[45] Date of Patent: Apr. 29, 1986

[54] 1,2,4,6-THIATRIAZINE 1,1-DIOXIDE ETHERS AND THEIR USE FOR CONTROLLING UNDESIRABLE PLANT GROWTH

[75] Inventors: Gerhard Hamprecht, Weinheim; Bruno Wuerzer, Otterstadt, both of Fed. Rep. of Germany

[73] Assignee: BASF Aktiengesellschaft, Fed. Rep. of Germany

[21] Appl. No.: 729,902

[22] Filed: May 6, 1985

Related U.S. Application Data

[63] Continuation of Ser. No. 524,661, Aug. 19, 1983, abandoned.

[30] Foreign Application Priority Data

Aug. 24, 1982 [DE] Fed. Rep. of Germany ....... 3231394

[51] Int. Cl.$^4$ ............... A01N 43/72; C07D 401/12; C07D 413/12; C07D 417/12
[52] U.S. Cl. ............................................. 71/91; 544/7
[58] Field of Search ................. 544/7; 260/273.3; 71/91

[56] References Cited

U.S. PATENT DOCUMENTS

| 4,013,447 | 3/1977 | Kay | 544/7 |
| 4,316,014 | 2/1982 | Hamprecht et al. | 544/7 |
| 4,343,648 | 8/1982 | Hamprecht et al. | 544/7 |
| 4,428,766 | 1/1984 | Hamprecht et al. | 544/7 |
| 4,497,810 | 2/1985 | Hoffman | 544/7 |

Primary Examiner—John M. Ford
Attorney, Agent, or Firm—Keil & Weinkauf

[57] ABSTRACT 1,2,4,6-Thiatriazine 1,1-dioxide ethers of the formula

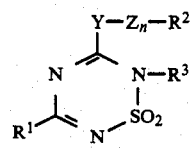

where $R^1$, $R^2$, $R^3$, Y, Z and n have the meanings given in the description, are used for controlling undesirable plant growth.

8 Claims, No Drawings

1,2,4,6-THIATRIAZINE 1,1-DIOXIDE ETHERS AND THEIR USE FOR CONTROLLING UNDESIRABLE PLANT GROWTH

This application is a continuation of application Ser. No. 524,661, filed on Aug. 19, 1983, now abandoned.

The present invention relates to 1,2,4,6-thiatriazine 1,1-dioxide ethers, herbicides which contain these compounds as active ingredients and their use for controlling undesirable plant growth.

It is known that substituted 6H-1,2,4,6-thiatriazin-5-one 1,1-dioxide derivatives have a herbicidal action (German Laid-Open Applications DOS 2,508,832, DOS 2,933,889 and DOS 3,016,825).

We have found that 1,2,4,6-thiatriazine 1,1-dioxide ethers of the formula

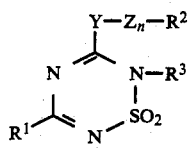

(I)

where $R^1$ is hydrogen, a saturated or unsaturated, straight-chain or branched aliphatic radical of not more than 10 carbon atoms or a saturated, straight-chain or branched aliphatic radical of not more than 10 carbon atoms which is substituted by halogen, alkoxy or alkylmercapto of 1 to 4 carbon atoms, or is alkyl- or dialkylamino where alkyl is of 1 to 6 carbon atoms, cycloalkyl of 3 to 7 carbon atoms or a radical $R^4$—X—, where $R^4$ has the meanings given for $R^1$, with the exception of alkyl- and dialkylamino, and X is oxygen, sulfur, —SO— or —SO$_2$—, $R^2$ is a 6-membered aromatic heterocyclic radical which contains 1 or 2 nitrogen atoms as ring members and is unsubstituted or substituted by alkyl of 1 to 4 carbon atoms, alkoxy of 1 to 4 carbon atoms, trifluoromethyl, cyano, nitro or halogen, or is a 5-membered aromatic heterocyclic radical which is unsubstituted or substituted by alkyl of 1 to 4 carbon atoms, alkoxy of 1 to 4 carbon atoms, trifluoromethyl, cyano, nitro or halogen and contains 1, 2 or 3 heteroatoms selected from the group consisting of oxygen, sulfur or nitrogen, with the proviso that the rings contain no more than one oxygen or one sulfur atom, or is a 5-membered or 6-membered benzofused aromatic heterocyclic radical which is unsubstituted or substituted by alkyl of 1 to 4 carbon atoms, alkoxy of 1 to 4 carbon atoms, trifluoromethyl, cyano, nitro or halogen and contains 1, 2 or 3 heteroatoms selected from the group consisting of oxygen, sulfur or nitrogen, with the proviso that the rings contain no more than one oxygen or one sulfur atom and n is 0, or is a non-aromatic 5-membered, 6-membered or 7-membered heterocyclic radical which is unsubstituted or substituted by alkyl of 1 to 4 carbon atoms, alkoxy of 1 to 4 carbon atoms, carbonyl or halogen, may or may not be benzofused and contains 1, 2 or 3 heteroatoms selected from the group consisting of oxygen, sulfur or nitrogen, with the proviso that the rings contain no more than 2 oxygen or 2 sulfur atoms, $R^3$ is hydrogen, a saturated or unsaturated, straight-chain or branched aliphatic radical of not more than 10 carbon atoms or a saturated, straight-chain or branched aliphatic radical of not more than 10 carbon atoms which is substituted by halogen or alkoxy of 1 to 4 carbon atoms, or is cycloalkyl of 3 to 7 carbon atoms, Y is oxygen, sulfur, —SO— or —SO$_2$—, Z is alkylene of 1 to 4 carbon atoms or —(CH$_2$)$_2$—O—CH$_2$—, —(CH$_2$)$_2$O— or —CH$_2$—CO—, and n is 0 or 1, have a substantial herbicidal action and are tolerated by crops.

In formula I, $R^1$ and $R^3$ are each hydrogen, a saturated of unsaturated, straight-chain or branched aliphatic radical of not more than 10 carbon atoms, eg. alkyl of not more than 10, preferably not more than 4, carbon atoms, or alkenyl or alkynyl of not more than 10, preferably not more than 4, carbon atoms, eg. methyl, ethyl, n-propyl, isopropyl, n-butyl, isobutyl, sec.-butyl, tert.-butyl, n-pentyl, tert.-amyl, n-hexyl, pent-3-yl, 1,2-dimethyl-n-propyl, 1,3-dimethyl-n-butyl, 1-ethyl-2-methyl-n-propyl, 1,2,2-trimethyl-n-propyl, hex-5-enyl, 1,2-dimethyl-4-hexyl, allyl, methallyl, crotyl, 2-ethylhex-2-enyl, 2-methylbut-2-enyl, 2-methylbut-3-enyl, but-1-en-3-yl, 2-methylbut-1-en-4-yl, 2-methylbut-2-en-4-yl, 3-methylbut-1-en-3-yl, propargyl, but-1-yn-3-yl or but-2-ynyl, or a saturated, straight-chain or branched aliphatic radical of not more than 10, preferably not more than 4, carbon atoms which is substituted by halogen or alkoxy of 1 to 4 carbon atoms, eg. haloalkyl of not more than 10, preferably 1 to 4, carbon atoms, or C$_1$–C$_4$-alkoxy-substituted alkyl of not more than 10, preferably not more than 4, carbon atoms, eg. 2-chloroethyl, 2-chloro-n-propyl, 3-chloro-n-propyl, 2-chlorosec.-butyl, 2-chloroisobutyl, 2-fluoro-sec.-butyl, 2-fluoroisobutyl, 2-fluoroisopropyl, chloro-tert.-butyl, 2,2,2-trifluoroethyl, 2-methoxyethyl, 2-ethoxyethyl, 3-methoxy-n-propyl, 2-methoxyisopropyl, 3-methoxy-n-butyl, 1-methoxy-sec.-butyl, methoxy-tert.-butyl, ethoxy-tert.-butyl, 2-methoxy-n-butyl or 4-methoxy n-butyl, or cycloalkyl of 3 to 7 carbon atoms, eg. cyclopropyl, cyclopentyl or cyclohexyl.

$R^1$ is furthermore alkyl- or dialkylamino where alkyl is of 1 to 6, preferably 1 to 4, carbon atoms, eg. methylamino, dimethylamino, ethylamino, isopropylamino, n-butylamino, methylethylamino or diisopropylamino, or is a saturated, straight-chain or branched aliphatic radical of not more than 10 carbon atoms which is substituted by alkylmercapto of 1 to 4 carbon atoms, for example alkyl of not more than 10, preferably 1 to 4, carbon atoms which is substituted by alkylmercapto of 1 to 4 carbon atoms, eg. 2-methylmercaptoethyl, 2-ethylmercaptoethyl, 3-methylmercapto-n-propyl, 3-methylmercapto-n-butyl, 1-methylmercaptosec.-butyl, methylmercapto-tert.-butyl or 2-methylmercapto-n-butyl.

In formula I, $R^2$ is a 6-membered aromatic heterocyclic radical which contains 1 or 2 nitrogen atoms and is unsubstituted or substituted by alkyl or alkoxy, each of 1 to 4 carbon atoms, trifluoromethyl, cyano, nitro or halogen, eg. radicals of the following heterocyclic structures: pyridine, 2-, 3- and 4-methylpyridine, 2-, 3- and 4-chloropyridine, 2-, 3- and 4-methoxypyridine, 2,3,4-trifluoromethylpyridine, 2-, 3- and 4-cyanopyridine, 2-, 3- and 4-nitropyridine, 3-chloro-5-trifluoromethylpyridine, 3,5-dichloropyridine, 3,5-dibromopyridine, 3,5-diiodopyridine, pyrimidine, 2-, 4- and 5-methylpyrimidine, 2,6-dimethylpyrimidine, 2-isopropyl-6-methylpyrimidine, 2-methyl-6-ethylpyrimidine, 2-, 4- and 5-chloropyrimidine, 2,4,5-trifluoromethylpyridine, 2-, 4- and 5-nitropyrimidine, 2-, 4- and 5-methoxypyrimidine, 2-, 4- and 5-cyanopyrimidine, 2,4-dichloropyrimidine, pyrazine, 2-methylpyrazine, 2-methoxypyrazine, 2-trifluoromethylpyrazine, 2-cyanopyrazine, 2-nitropyrazine, 2-chloropyrazine, 2,5-dichloropyrazine, pyridazine, 3- and 4-methylpyridazine, 3,6-dimethylpyridazine, 3- and 4-chloropyridazine and 3,6-dichloropyridazine, or is a 5-membered aromatic heterocyclic radical which is unsubstituted or substituted by alkyl of 1 to 4 carbon atoms, alkoxy of 1 to 4 carbon atoms, trifluoromethyl, cyano, nitro or halogen and contains 1, 2 or 3 heteroatoms selected from the group consisting of oxygen, sulfur or nitrogen, with the proviso that the rings contain no more than one oxygen or one sulfur atom, for example radicals of the following heterocyclic structures: furan, 2- and 3-chlorofuran, 2- and 3-methylfuran, 2- and 3-methoxyfuran, 2- and 3-nitrofuran, 2,3-dichlorofuran, 2,5-dichlorofuran, 2,5-dimethylfuran, thiophene, 2- and 3-methylthiophene, 2- and 3-methoxythiophene, 2- and 3-nitrothiophene, 2,3-dichlorothiophene, 2,5-dichlorothiophene, 2,5-dimethylthiophene, 2- and 3-chloropyrrole, 1-, 2- and 3-methylpyrrole, 2,3-dichloropyrrole, 2,5-dichloropyrrole, 2,5-dimethylpyrrole, oxazole, 2-, 4- and 5-methyloxazole, 2-, 4- and 5-methoxyoxazole, 2,4,5-chloroxazole, 2,4,5-imidazole, 1-, 2-, 4- and 5-methylimidazole, 4- and 5-nitroimidazole, 2,4-dimethylimidazole, 4,5-dichloroimidazole, 4,5-chloroimidazole, pyrazole, 1-, 3- and 4-methylpyrazole, 3,4-chloropyrazole, 3- and 4-nitropyrazole, 2-, 4- and 5-thiazole, 2-, 4- and 5-methylthiazole, 2-, 4- and 5-methoxythiazole, 2-, 4- and 5-chlorothiazole, isothiazole, 3-, 4- and 5-methylisothiazole, isoxazole, 3-, 4- and 5-methylisoxazole, 1-, 4- and 5-methyl-1,2,3-triazole, 1,2,3-triazole, 1,3,4-triazole, 1,2,4-triazole, 2-methyl-1,3,4-triazole, 1,3,4-oxadiazole, 2-methyl-1,3,4-oxadiazole, 1,2,3-oxadiazole, 4- and 5-methyl-1,2,3-oxadiazole, 1,2,3-thiadiazole, 4- and 5-methyl-1,2,3-thiadiazole, 4- and 5-chloro-1,2,3-thiadiazole, 1,2,5-oxadiazole, 3- and 4-methyl-1,2,5-oxadiazole, 1,2,5-thiadiazole and 3- and 4-methyl-1,2,5-thiadiazole, or is a 5-membered or 6-membered benzofused aromatic heterocyclic radical which is unsubstituted or substituted by alkyl of 1 to 4 carbon atoms, alkoxy of 1 to 4 carbon atoms, trifluoromethyl, cyano, nitro or halogen and contains 1, 2 or 3 heteroatoms selected from the group consisting of oxygen, sulfur or nitrogen, with the proviso that the rings contain no more than one oxygen or one sulfur atom and n is 0, for example radicals of the following heterocyclic structures: benzoxazole, 2-, 4-, 5-, 6- and 7-chlorobenzoxazole, 2-, 4-, 5-, 6- and 7-trifluoromethylbenzoxazole, 2-, 4-, 5-, 6- and 7-nitrobenzoxazole, 2-, 4-, 5-, 6- and 7-methylbenzoxazole, benzimidazole, 2-, 4-, 5-, 6- and 7-methylbenzimidazole, 2-, 4-, 5-, 6- and 7-chlorobenzimidazole, 2-, 4-, 5-, 6- and 7-trifluoromethylbenzimidazole, benzothiazole, 2-, 4-, 5-, 6- and 7-chlorobenzothiazole, 2-, 4-, 5-, 6- and 7-trifluoromethylbenzothiazole, 2-, 4-, 5-, 6- and 7-nitrobenzothiazole, benzofuran, 3,3-dimethyl-2-methoxybenzofuran, 2-, 3-, 4-, 5-, 6- and 7-chlorobenzofuran, 2-, 3-, 4-, 5-, 6- and 7-methylbenzofuran, indole, 1-, 2-, 3-, 4-, 5-, 6- and 7-methylindole, 1-, 3-, 4-, 5-, 6- and 7-methylbenzopyrazole, benzisoxazole, 3-, 4-, 5-, 6- and 7-chlorobenzisoxazole, 3-, 4-, 5-, 6- and 7-methylbenzisoxazole, 3-, 4-, 5-, 6- and 7-trifluoromethylbenzisoxazole, benzisothiazole, 3-, 4-, 5-, 6- and 7-methylbenziosthiazole, 3-, 4-, 5-, 6- and 7-chlorobenzisothiazole, benzotriazole, 4-, 5-, 6- and 7-chlorobenzotriazole, benzothiophene, benzo-1,2,3-thiadiazole, 4-, 5-, 6- and 7-chlorobenzo-2,3-thiadiazole, 4-, 5-, 6- and 7-methylbenzo-1,2,3-thiadiazole, benzo-2,1,3-thiadiazole, 4-, 5-, 6- and 7-chlorobenzo-2,1,3-thiadiazole, 4-, 5-, 6- and 7-methylbenzo-2,1,3-thiadiazole, quinoline, 2-, 3-, 4-, 5-, 6-, 7- and 8-chloroquinoline, 5,7-dichloroquinoline, 5,7-dibromoquinoline, 3,5-dichloroquinoline, 3,5,7-trichloroquinoline, 5-chloro-7-bromoquinoline, 5-nitro-7-chloroquinoline, isoquinoline, 1-, 3-, 4-, 5-, 6-, 7- and 8-methylisoquinoline, 1-, 3-, 4-, 5-, 6-, 7- and 8-chloroisoquinoline, benzopyrimidine, 2-, 4-, 5-, 6-, 7- and 8-methylbenzopyrimidine, 2-, 4-, 5-, 6-, 7- and 8-chlorobenzopyrimidine, 2-, 4-, 5-, 6-, 7- and 8-trifluoromethylbenzopyrimidine, cinnoline, 3-, 4-, 5-, 6-, 7- and 8-chlorocinnoline, 3-, 4-, 5-, 6-, 7- and 8-methylcinnoline, quinoxaline, 2-, 3-, 4-, 5-, 6-, 7- and 8-chloroquinoxaline, 2-, 3-, 4-, 5-, 6-, 7- and 8-trifluoromethylquinoxaline, 2-, 3-, 4-, 5-, 6-, 7- and 8-methylquinoxaline, benzo-1,2,4-triazine, 3-, 5-, 6-, 7- and 8-chlorobenzo-1,2,4-triazine and 3-, 5-, 6-, 7- and 8-methylbenzo-1,2,4-triazine, or is a 5-membered, 6-membered or 7-membered non-aromatic heterocyclic radical which is unsubstituted or substituted by alkyl of 1 to 4 carbon atoms, alkoxy of 1 to 4 carbon atoms, carbonyl or halogen, may or may not be benzofused and contains 1, 2 or 3 heteroatoms selected from the group consisting of oxygen, sulfur or nitrogen, with the proviso that the rings contain no more than 2 oxygen or 2 sulfur atoms, for example radicals of the following heterocyclic structures: dihydrofuran, tetrahydrofuran, 2- and 3-methoxyfuran, 2,5-dimethoxyfuran, 2- and 3-chlorotetrahydrofuran, pyrroline, 1-, 2- and 3-methylpyrroline, pyrrolidine, 1-, 2- and 3-methylpyrrolidine, pyrrolidone, 1-methylpyrrolidone, tetrahydrothiophene, sulfolane, 1,3-dioxane, 1,4-dioxane, piperidine, 1-methylpiperidine, piperidone, 1-methylpiperidone, piperazine, 1-methylpiperazine, hexamethyleneimine, caprolactam, dihydro-, tetrahydro- and hexahydropyrimidine, 1-methylhexahydropyrimidine, pyridaz-6-one, 1-methylpyridaz-6-one, 2,4-dichloropyridaz-6-one, 1-phenylpyridaz-6-one, pyran, 2-, 3-, 4-, 5- and 6-methylpyran, 2,4,5,6-chloropyran, α-pyrone, 3,4,5,6-methyl-α-pyrone, 3-, 4-, 5- and 6-methyl-α-pyrone, γ-pyrone, 2- and 3-methyl-γ-pyrone, 2- and 3-chloro-γ-pyrone, 1,2,3-, 1,2,4- and 1,3,5-triazine, 1,2,4-oxazine, 1,3,6-oxazine, 1,3,2-oxazine, 1,2,6-oxazine, 1,4-oxazine, o-isoxazine, p-isoxazine, 1,2,5-oxathiazine, 1,4,2-oxadiazine, 1,3,5,2-oxadiazine, morpholine, 2,3,4-methylmorpholine, azepine, 1,2,4-diazepine, 1,2-benzopyran, coumarin, chromane, isocoumarin, 1,3-benzopyrone, 3,4,5,6-methyl-1,2-pyrone, 1,3,2-benzoxazine, isobenzofuran, anthranil, 1,4,2-benzoxazine, 2,3,1-benzoxazine, 3,1,4-benzoxazine, 1,2-benzisoxazine, 1,4-benzisoxazine and 3,4,5,6,7,8-methylbenzo-1,2-pyrone.

Preferred compounds of the formula I are those in which $R^1$ is alkyl of 1 to 4 carbon atoms or a radical $R^4$—X—, where $R^4$ is alkyl of 1 to 4 carbon atoms and X is oxygen, $R^2$ is a free or benzofused pyridine, radical which is unsubstituted or substituted by methyl, nitro or chlorine, $R^3$ is alkyl of not more than 4 carbon atoms, Y is oxygen, Z is methylene and n is 0 or 1, or those in which $R^1$ is alkyl of 1 to 4 carbon atoms or a radical $R^4$—X—, where $R^4$ is alkyl of 1 to 4 carbon atoms and X is oxygen, $R^2$ is a free or benzofused pyrimidine, pyran, oxazole, thiazole, isoxazole, thiophene, furan, dihydrofuran, tetrahydrofuran, pyrrole, pyrrolidine, piperidine, hexamethyleneimine, 1,4-dioxane or 1,2,3-thiadiazole radical which is substituted by alkyl or alkoxy, each of 1 to 4 carbon atoms, or by halogen, $R^3$ is alkyl of 1 to 4 carbon atoms, Y is oxygen or sulfur, Z is methylene and n is 0 or 1, or those in which $R^1$ is alkyl of 1 to 4 carbon atoms or a radical $R^4$—X—, where $R^4$ is alkyl of 1 to 4 carbon atoms and X is oxygen, $R^2$ is a tetrahydrofuran, pyrrolidine, piperidine or hexamethyleneimine radical which is substituted by carbonyl, lower alkyl or lower alkoxy, $R^3$ is alkyl of 1 to 4 carbon atoms, Y is oxygen or sulfur, Z is alkylene of 2 to 4 carbon atoms or $(CH_2)_2O-CH_2$, $-(CH_2)_2O-$ or

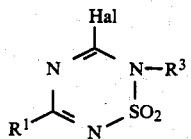 (II)

and n is 1, or those which $R^1$ is a radical $R^4-X-$, where $R^4$ is methyl and X is oxygen, $R^2$ is pyridyl, methylpyridyl, quinolyl, 1,2,3-thiadiazolyl, furyl, tetrahydrofuranyl, 2,5-dimethoxytetrahydrofuranyl, 2-bromothienyl, 2,5-dichlorothienyl, 3-methylisoxazolyl, benzo-1,4-dioxanyl, pyrrolid-2-onyl, 2-isopropyl-6-methylpyrimidinyl, benzothiazol-2-yl, benzoxazol-2-yl or 1-(2,3-dimethylhexamethyleneimino), $R^3$ is methyl, Y is oxygen or sulfur, Z is methylene, dimethylene or $-CH_2-CO-$, $-(CH_2)_2-O-$ or $-(CH_2)_2-O-CH_2$ and n is 0, 1 or 2.

The 1,2,4,6-thiatriazine 1,1-dioxide ethers of the formula I are obtained by a method in which a compound of the formula

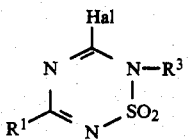 (II)

where $R^1$ and $R^3$ have the above meanings and Hal is halogen, is reacted with a compound of the formula

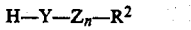  (III)

where $R^2$, Y, Z and n have the above meanings, or with an alkali metal salt, alkaline earth metal salt or ammonium salt of a compound of the formula III in the presence or absence of an inert organic solvent and in the presence or absence of an acid acceptor at from $-50°$ to $+150°$ C. under atmospheric or superatmospheric pressure, either continuously or batchwise.

If 3-chloro-5-methyl-2-isopropyl-2H-1,2,4,6-thiatriazine 1,1-dioxide and 3-hydroxypyridine are used as starting materials, the course of the reaction can be represented by the following equation:

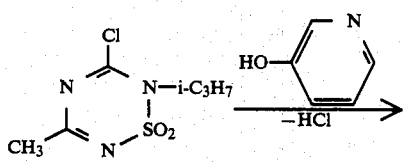

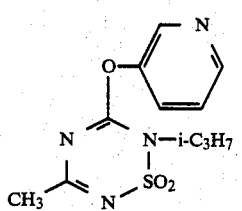

If 5-chloro-6-isopropyl-3-methoxy-6H-1,2,4,6-thiatriazine 1,1-dioxide and 2-mercaptomethylfuran are used as starting materials, the course of the reaction can be represented by the following equation:

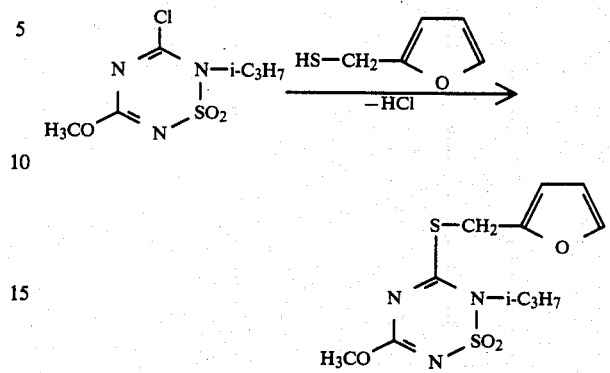

Advantageously, the reaction is carried out using solvents or diluents which are inert under the particular reaction conditions. Examples of suitable solvents are halohydrocarbons, in particular chlorohydrocarbons, eg. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- or p-difluorobenzene, 1,2-dichloroethane, 1,1-dichloroethane, 1,2-cis-dichloroethylene, chlorobenzene, fluorobenzene, iodobenzene, o-, m- or p-dichlorobenzene, o-, m or p-dibromobenzene, o-, m- or p-chlorotoluene or 1,2,4-trichlorobenzene; ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole or $\beta,\beta'$-dichlorodiethyl ether; nitrohydrocarbons, eg. nitromethane, nitroethane, nitrobenzene, o-, m- or p-chloronitrobenzene or o-nitrotoluene; nitriles, eg. acetonitrile, butyronitrile, isobutyronitrile, benzonitrile or m-chlorobenzonitrile; aliphatic or cycloaliphatic hydrocarbons, eg. heptane, pinane, nonane, o-, m- or p-cymene, gasoline fractions, boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane or octane; esters, eg., ethyl acetate, ethyl acetoacetate or isobutyl acetate; amides, eg. formamide, methylformamide or dimethylformamide; ketones, eg. acetone or methyl ethyl ketone, and if appropriate water and mixtures of these solvents. Advantageously, the solvent is used in an amount of from 100 to 2,000, preferably from 200 to 700, % by weight, based on starting material II.

The acid acceptor used can be any conventional one. Such acid acceptors preferably include tertiary amines, alkaline earth metal compounds, ammonium compounds and alkali metal compounds, as well as mixtures of these. Zinc compounds may also be used. Examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-di-methylaniline, N,N-diethylaniline, N,N-dipropylaniline, N,N-dimethyltoluidine, N,N-diethyltoluidine, N,N-dipropyl-toluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, isoquinoline, pyrimidine, acridine, N,N,N',N'-tetramethylethylenediamine N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine.

Advantageously, the acid acceptor is used in an amount of from 80 to 120%, based on starating material II, of the stoichiometric amount required. However, it is also possible to remove the resulting hydrogen halide by flushing the mixture with an inert gas, eg. nitrogen.

The starting material III required for the reaction is generally employed in an amount of from 80 to 120%, based on starting material II, of the stoichiometric amount required. However, starting material III can also be used directly as the solvent.

Advantageously, the process for the preparation of the novel compounds is carried out as follows: the starting material II, if appropriate in one of the above diluents, is initially introduced and the starting material III and an acid acceptor are then added simultaneously or in succession. However, it is also possible initially to introduce starting material III in one of the above diluents and then to add starting material II and an acid acceptor, simultaneously or in any desired sequence, via two separate feeds.

In many cases, the reaction is complete as soon as the components have been introduced; in other cases, stirring is continued for from 10 minutes to 10 hours at from −50° to 150° C., preferably from 0° to 120° C., in particular from 10° to 50° C., to complete the reaction.

If an inert gas is used to remove the hydrogen halide, it is advantageous to continue stirring the mixture for from 0.2 to 10 hours at from 40° to 100° C.

The end product I is isolated from the reaction mixture in a conventional manner, for example after the solvent or excess starting material III has been distilled off, or directly by filtration under suction. In this case, the residue which remains is washed with water or diluted alkali to remove acidic impurities, and is dried. In the case of water-immiscible diluents, the reaction mixture can also be extracted directly with water or with a dilute alkali, and the organic phase can then be dried and evaporated down. However, it is also possible to dissolve the residue in a water-immiscible solvent and to wash the solution as described above. The desired end products are obtained in a pure form; if required, they can be purified by recrystallization, chromatography or distillation.

EXAMPLE 1

2,5-Dimethyl-3-(pyrid-3-yloxy)-2H-1,2,4,6-thiatriazine 1,1-dioxide 17.1 parts of β-hydroxypyridine in 120 parts of methylene chloride and 19.1 parts of N,N-dimethylcyclohexylamine are introduced simultaneously, via 2 feeds, in the course of 15 minutes and at 15°–20° C., into a stirred solution of 29.3 parts of 2,5-dimethyl-3-chloro-2H-1,2,4,6-thiatriazine 1,1-dioxide in 150 parts of methylene chloride. The mixture is stirred for one hour at 25° C., after which the precipitate is filtered off under suction and the filtrate is washed with water and with dilute sodium carbonate solution, dried over magnesium sulfate, chromatographed over neutral aluminum oxide and then evaporated down under reduced pressure to give 26 parts (68.6% of theory) of 2,5-dimethyl-3-(pyrid-3-yloxy)-2H-1,2,4,6-thiatriazine 1,1-dioxide of melting point 137°–138° C. (compound No. 1).

EXAMPLE 2

6l-Ethyl-3-methoxy-5-(5-chloroquinolyl-8-oxy)-6H-1,2,4,6-thiatriazine 1,1-dioxide 21.5 parts of 5-chloro-8-hydroxyquinoline in 150 parts of 1,2-dichloroethane and 12.4 parts of triethylamine are added simultaneously in the course of 10 minutes to 22.6 parts of 6-ethyl-3-methoxy-5-chloro-6H-1,2,4,6-thiatriazine 1,1-dioxide in 70 parts of 1,2-dichloroethane at from 20° to 25° C., while stirring. The reaction mixture is then stirred for 3 hours at 40° C., cooled, washed in succession with water, 1N hydrochloric acid and dilute sodium carbonate solution, dried over magnesium sulfate and evaporated down under reduced pressure to give 28.8 parts (79% of theory) of 6-ethyl-3-methoxy-5-(5-chloroquinolyl-8-oxy)-6H-1,2,4,6-thiatriazine 1,1-dioxide of melting point 206°–207° C. (compound No. 2).

EXAMPLE 3

6-Methyl-3-methoxy-5-(1-methylpyridaz-6-on-3-yloxy)-6H-1,2,4,6-thiatriazine 1,1-dioxide 25.3 parts of 6-methyl-3-methoxy-5-chloro-6H-1,2,4,6-thiatriazine 1,1-dioxide in 50 parts of ethyl acetate and a mixture of 13.9 parts of 1-methyl-3-hydroxypyridaz-6-one and 13.3 parts of dimethylaniline in 125 parts of ethyl acetate are introduced uniformly, via 2 feeds, into a stirred apparatus in the course of 20 minutes at from 15° to 20° C. The reaction mixture is stirred for one and a half hours at 25° C., after which the product is filtered off under suction, washed with 30 parts of ethyl acetate, with water and then with dilute sodium carbonate solution and dried under reduced pressure to give 22.5 parts (62% of theory) of 6-methyl-3-methoxy-5-(1-methylpyridaz-6-on-3-yloxy)-6H-1,2,4,6-thiatriazine 1,1-dioxide of melting point 206°–210° C. (compound No. 3).

The compounds shown in the Table are obtained by methods similar to those described in the above Examples.

| Compound no. | $R^4$ | X | Y | Z | $R^2$ | $R^3$ | M.p. [°C.] $n_D^{25}$ |
|---|---|---|---|---|---|---|---|
| 4 | $CH_3$ | O | O | — | pyrid-2-yl | | H |

-continued

| Compound no. | R⁴ | X | Y | Z | R² | R³ | M.p. [°C.] $n_D^{25}$ |
|---|---|---|---|---|---|---|---|
| 5 | CH₃ | O | O | — | pyrid-2-yl | CH₃ | 138–141 |
| 6 | CH₃ | O | O | — | pyrid-2-yl | H | |
| 7 | CH₃ | O | O | — | pyrid-3-yl | H | |
| 8 | CH₃ | O | O | — | pyrid-3-yl | CH₃ | 165–168 |
| 9 | H | O | O | — | pyrid-3-yl | CH₃ | |
| 10 | CH₃ | O | S | — | pyrid-3-yl | H | |
| 11 | CH₃ | O | O | — | pyrid-4-yl | H | |
| 12 | CH₃ | O | O | — | pyrid-4-yl | CH₃ | 120 |
| 13 | CH₃ | O | O | — | 3-methylpyrid-2-yl | CH₃ | |
| 14 | CH₃ | O | O | — | 3-methylpyrid-4-yl | CH₃ | |
| 15 | CH₃ | O | O | — | 3-methylpyrid-5-yl | CH₃ | |
| 16 | CH₃ | O | O | — | 3-methylpyrid-6-yl | CH₃ | |
| 17 | CH₃ | O | O | — | 2-methylpyrid-3-yl | CH₃ | |
| 18 | CH₃ | O | O | — | 2-methylpyrid-4-yl | CH₃ | |
| 19 | CH₃ | O | O | — | 2-methylpyrid-5-yl | CH₃ | 155–158 |
| 20 | CH₃ | O | O | — | 2-methylpyrid-6-yl | CH₃ | 148–150 |
| 21 | CH₃ | O | O | — | 4-methylpyrid-2-yl | CH₃ | |
| 22 | CH₃ | O | O | — | 4-methylpyrid-3-yl | CH₃ | |
| 23 | CH₃ | — | O | — | 2-methylpyrid-5-yl | CH₃ | |
| 24 | CH₃ | O | O | — | pyrid-4-yl | C₂H₅ | 134 |
| 25 | CH₃ | S | O | — | 3-methylpyrid-2-yl | CH₃ | |
| 26 | CH₃ | O | O | — | 3-methylpyrid-4-yl | H | |
| 27 | H | O | O | — | 3-methylpyrid-5-yl | CH₃ | |
| 28 | CH₃ | O | S | — | 3-methylpyrid-6-yl | CH₃ | |
| 29 | CH₃ | S | O | — | 2-methylpyrid-3-yl | CH₃ | |
| 30 | CH₃ | O | O | — | 2-methylpyrid-4-yl | H | |
| 31 | H | O | O | — | 2-methylpyrid-5-yl | CH₃ | |
| 32 | CH₃ | O | S | — | 2-methylpyrid-6-yl | CH₃ | |
| 33 | CH₃ | O | O | — | 2-chloropyrid-3-yl | H | |
| 34 | CH₃ | O | O | — | 2-chloropyrid-4-yl | CH₃ | |
| 35 | CH₃ | O | O | — | 2-chloropyrid-5-yl | CH₃ | |
| 36 | CH₃ | O | O | — | 2-chloropyrid-6-yl | CH₃ | 139–142 |
| 37 | CH₃ | O | O | — | 3-chloropyrid-2-yl | CH₃ | |
| 38 | CH₃ | O | O | — | 3-chloropyrid-4-yl | CH₃ | |
| 39 | CH₃ | O | O | — | 3-chloropyrid-5-yl | CH₃ | 131–132 |
| 40 | CH₃ | O | O | — | 3-chloropyrid-6-yl | CH₃ | 141–146 |
| 41 | CH₃ | O | O | — | 4-chloropyrid-2-yl | CH₃ | |
| 42 | CH₃ | O | O | — | 4-chloropyrid-3-yl | CH₃ | |
| 43 | C₂H₅ | O | O | — | 3-chloropyrid-5-yl | CH₃ | 146–148 |
| 44 | CH₃ | S | O | — | 3-chloropyrid-6-yl | CH₃ | |
| 45 | CH₃ | O | S | — | 2-chloropyrid-3-yl | CH₃ | |
| 46 | CH₃ | S | O | — | 2-chloropyrid-4-yl | CH₃ | |
| 47 | CH₃ | O | O | — | 2-methoxypyrid-3-yl | CH₃ | |
| 48 | CH₃ | O | O | — | 2-methoxypyrid-4-yl | CH₃ | |
| 49 | CH₃ | O | O | — | 2-methoxypyrid-5-yl | CH₃ | |
| 50 | CH₃ | O | O | — | 2-methoxypyrid-6-yl | CH₃ | |
| 51 | CH₃ | O | O | — | 3-methoxypyrid-2-yl | CH₃ | |
| 52 | CH₃ | O | O | — | 3-methoxypyrid-4-yl | CH₃ | |
| 53 | CH₃ | O | O | — | 3-methoxypyrid-5-yl | CH₃ | |
| 54 | CH₃ | O | O | — | 3-methoxypyrid-6-yl | CH₃ | |
| 55 | CH₃ | O | O | — | 4-methoxypyrid-2-yl | CH₃ | |
| 56 | CH₃ | O | O | — | 4-methoxypyrid-3-yl | CH₃ | |
| 57 | CH₃ | O | O | — | 3,5-dichloropyrid-2-yl | CH₃ | |
| 58 | CH₃ | O | O | — | 3-chloro-5-trifluoromethylpyrid-2-yl | CH₃ | |
| 59 | CH₃ | O | O | — | 2-trifluoromethylpyrid-3-yl | CH₃ | |
| 60 | CH₃ | O | O | — | 2-trifluoromethylpyrid-4-yl | CH₃ | |
| 61 | CH₃ | O | O | — | 2-trifluoromethylpyrid-5-yl | CH₃ | |
| 62 | CH₃ | O | O | — | 2-trifluoromethylpyrid-6-yl | CH₃ | |
| 63 | CH₃ | O | O | — | 2-methoxypyrid-6-yl | H | |
| 64 | CH₃ | O | S | — | 2-methoxypyrid-6-yl | CH₃ | |
| 65 | CH₃ | O | O | — | 3-trifluoromethylpyrid-2-yl | CH₃ | |
| 66 | CH₃ | O | O | — | 3-trifluoromethylpyrid-4-yl | CH₃ | |
| 67 | CH₃ | O | O | — | 3-trifluoromethylpyrid-5-yl | CH₃ | |
| 68 | CH₃ | O | O | — | 3-trifluoromethylpyrid-6-yl | CH₃ | |
| 69 | CH₃ | O | O | — | 4-trifluoromethylpyrid-2-yl | CH₃ | |
| 70 | CH₃ | O | O | — | 4-trifluoromethylpyrid-3-yl | CH₃ | |
| 71 | CH₃ | O | O | — | 2-cyanopyrid-3-yl | CH₃ | |
| 72 | CH₃ | O | O | — | 2-cyano-pyrid-4-yl | CH₃ | |
| 73 | CH₃ | O | O | — | 2-cyano-5-yl | CH₃ | |
| 74 | CH₃ | O | O | — | 2-cyanopyrid-6-yl | CH₃ | |
| 75 | CH₃ | O | O | — | 3-cyanopyrid-2-yl | CH₃ | |
| 76 | CH₃ | O | O | — | 3-cyanopyrid-4-yl | CH₃ | |
| 77 | CH₃ | O | O | — | 3-cyanopyrid-5-yl | CH₃ | |
| 78 | CH₃ | O | O | — | 3-cyanopyrid-6-yl | CH₃ | |
| 79 | CH₃ | O | O | — | 4-cyanopyrid-2-yl | CH₃ | |
| 80 | CH₃ | O | O | — | 4-cyanopyrid-3-yl | CH₃ | |
| 81 | CH₃ | — | O | — | 3-nitropyrid-6-yl | CH₃ | |
| 82 | CH₃ | O | O | — | 2-nitropyrid-3-yl | CH₃ | |
| 83 | CH₃ | O | O | — | 2-nitropyrid-4-yl | CH₃ | |
| 84 | CH₃ | O | O | — | 2-nitropyrid-5-yl | CH₃ | |

-continued

| Compound no. | R⁴ | X | Y | Z | R² | R³ | M.p. [°C]/ $n_D^{25}$ |
|---|---|---|---|---|---|---|---|
| 85 | CH₃ | O | O | — | 2-nitropyrid-6-yl | CH₃ | |
| 86 | CH₃ | O | O | — | 3-nitropyrid-2-yl | CH₃ | |
| 87 | CH₃ | O | O | — | 3-nitropyrid-4-yl | CH₃ | |
| 88 | CH₃ | O | O | — | 3-nitropyrid-5-yl | CH₃ | |
| 89 | CH₃ | O | O | — | 3-nitropyrid-6-yl | CH₃ | 147–150 |
| 90 | CH₃ | O | O | — | 4-nitropyrid-2-yl | CH₃ | |
| 91 | CH₃ | O | O | — | 4-nitropyrid-3-yl | CH₃ | |
| 92 | CH₃ | O | O | — | 3,5-diiodopyrid-2-yl | CH₃ | |
| 93 | CH₃ | — | O | — | 3,5-dibromopyrid-2-yl | CH₃ | |
| 94 | CH₃ | — | O | — | 3-chloro-5-trifluoromethyl-pyrid-2-yl | CH₃ | |
| 95 | CH₃ | O | O | — | pyrimidin-2-yl | CH₃ | |
| 96 | CH₃ | O | O | — | pyrimidin-4-yl | CH₃ | |
| 97 | CH₃ | O | O | — | pyrimidin-5-yl | CH₃ | |
| 98 | CH₃ | O | O | — | 2-methylpyrimidin-4-yl | CH₃ | |
| 99 | CH₃ | O | O | — | 2,6-dimethylpyrimidin-4-yl | CH₃ | |
| 100 | CH₃ | O | O | CH₂ | pyrid-2-yl | CH₃ | 105–108 |
| 101 | CH₃ | O | O | CH₂ | pyrid-3-yl | CH₃ | |
| 102 | CH₃ | O | O | CH₂ | pyrid-4-yl | CH₃ | |
| 103 | CH₃ | — | O | CH₂ | pyrid-2-yl | CH₃ | |
| 104 | (CH₃)₂N | — | O | CH₂ | pyrid-2-yl | CH₃ | |
| 105 | CH₃ | — | O | CH₂ | pyrid-3-yl | CH₃ | |
| 106 | CH₃ | — | O | CH₂ | pyrid-4-yl | CH₃ | |
| 107 | CH₃ | O | O | — | 1-methyl-pyridaz-6-on-3-yl | C₂H₅ | |
| 108 | CH₃ | O | O | CH₂ | 4,5-dichloropyridaz-6-on-yl | CH₃ | 156–159 |
| 109 | CH₃ | O | O | — | 4-methylpyrimidin-2-yl | CH₃ | |
| 110 | CH₃ | O | S | — | pyrimidin-2-yl | CH₃ | |
| 111 | CH₃ | O | O | — | 2-isopropyl-6-methyl-pyrimidin-4-yl | CH₃ | 88–91 |
| 112 | CH₃ | O | O | — | pyrazin-2-yl | CH₃ | |
| 113 | CH₃ | O | O | — | 5-chloropyrazin-2-yl | CH₃ | |
| 114 | CH₃ | O | O | — | 5-methylpyrazin-2-yl | CH₃ | |
| 115 | CH₃ | O | O | — | fur-2-yl | CH₃ | |
| 116 | CH₃ | O | O | — | fur-3-yl | CH₃ | |
| 117 | CH₃ | O | O | CH₂ | tetrahydrofuran-2-yl | CH₃ | 65–68 |
| 118 | CH₃ | — | O | CH₂ | tetrahydrofuran-3-yl | CH₃ | |
| 119 | CH₃ | O | O | CH₂ | 2,5-dimethyoxy-tetrahydrofuran-3-yl | CH₃ | 1.4992 |
| 120 | CH₃ | O | O | — | thien-2-yl | CH₃ | |
| 121 | CH₃ | O | O | — | thien-3-yl | CH₃ | |
| 122 | (CH₃)₂N | — | O | CH₂ | tetrahydrofuran-2-yl | CH₃ | |
| 123 | CH₃ | O | O | — | 2-methylfuran-3-yl | CH₃ | |
| 124 | CH₃ | O | O | — | 3-methylthien-2-yl | CH₃ | |
| 125 | CH₃ | O | O | — | pyrrol-2-yl | CH₃ | |
| 126 | CH₃ | O | O | — | 1-methylpyrrol-3-yl | CH₃ | |
| 127 | CH₃ | O | O | (CH₂)₂ | 1-methylpiperazin-4-yl | CH₃ | |
| 128 | CH₃ | O | O | CH₂ | 1-methylpiperazin-4-yl | CH₃ | |
| 129 | CH₃ | O | O | CH₂—CH(CH₃) | 1,3-dioxan-2-yl | CH₃ | 70–71 |
| 130 | CH₃ | — | O | CH₂—CH(CH₃) | 1,3-dioxan-2-yl | CH₃ | |
| 131 | CH₃ | O | O | (CH₂)₂—O—CH₂ | tetrahydrofuran-2-yl | CH₃ | 1.5030 |
| 132 | CH₃ | — | O | —(CH₂)₂—O—CH₂— | tetrahydrofuran-2-yl | CH₃ | |
| 133 | (CH₃)₂N | — | O | —CH₂—CH(CH₃)— | 1,3-dioxan-2-yl | CH₃ | |
| 134 | CH₃ | O | O | CH₂ | morpholin-4-yl | CH₃ | |
| 135 | CH₃ | O | O | (CH₂)₂ | morpholin-4-yl | CH₃ | |
| 136 | CH₃ | O | O | CH₂ | piperidinyl- | CH₃ | |
| 137 | CH₃ | O | O | (CH₂)₂ | piperidinyl- | CH₃ | |
| 138 | CH₃ | O | O | CH₂ | piperidin-2-on-1-yl | CH₃ | |
| 139 | CH₃ | O | O | (CH₂)₂ | piperidin-2-on-1-yl | CH₃ | |
| 140 | CH₃ | — | O | (CH₂)₂ | piperidin-2-on-1-yl | CH₃ | |
| 141 | CH₃ | O | O | CH₂ | pyrrolidinyl | CH₃ | |
| 142 | CH₃ | — | O | CH₂ | pyrrolid-2-on-1-yl | CH₃ | |
| 143 | CH₃ | O | O | (CH₂)₂ | pyrrolid-2-on-1-yl | CH₃ | 133–136 |
| 144 | CH₃ | O | O | (CH₂)₂ | pyrrolidinyl | CH₃ | |
| 145 | CH₃ | O | O | (CH₂)₂ | 3-ethylpyrid-2-yl | CH₃ | |
| 146 | CH₃ | O | O | — | tetrahydrothiophen-3-yl | CH₃ | |
| 147 | CH₃ | O | O | — | pyrazol-3-yl | CH₃ | |
| 148 | CH₃ | O | O | — | pyrazol-4-yl | CH₃ | |
| 149 | CH₃ | O | O | — | isoxazol-3-yl | CH₃ | |
| 150 | CH₃ | O | O | — | isoxazol-4-yl | CH₃ | |
| 151 | CH₃ | O | O | — | isoxazol-5-yl | CH₃ | |
| 152 | CH₃ | O | O | — | isothiazol-3-yl | CH₃ | |
| 153 | CH₃ | O | O | — | isothiazol-4-yl | CH₃ | |
| 154 | CH₃ | O | O | — | imidazol-2-yl | CH₃ | |
| 155 | CH₃ | O | O | — | imidazol-4-yl | CH₃ | |
| 156 | CH₃ | O | O | (CH₂)₂O | tetrahydrofuran-3-yl | CH₃ | 128–130 |

-continued

| Compound no. | R⁴ | X | Y | Z | R² | R³ | M.p. [°C] $n_D^{25}$ |
| --- | --- | --- | --- | --- | --- | --- | --- |
| 157 | CH₃ | O | O | — | oxazol-2-yl | CH₃ | |
| 158 | CH₃ | O | O | — | oxazol-4-yl | CH₃ | |
| 159 | CH₃ | O | O | — | thiazol-2-yl | CH₃ | |
| 160 | CH₃ | O | O | — | thiazol-4-yl | CH₃ | |
| 161 | CH₃ | O | O | — | quinolin-8-yl | CH₃ | 213–216 |
| 162 | CH₃ | O | O | CH₂ | imidazolyl | CH₃ | |
| 163 | CH₃ | O | O | (CH₂)₂ | imidazolyl | CH₃ | |
| 164 | CH₃ | O | O | — | 5-chloroquinolin-8-yl | CH₃ | 190–193 |
| 165 | CH₃ | — | O | — | 5-chloroquinolin-8-yl | CH₃ | 206–212 |
| 166 | CH₃ | O | O | — | 5,7-dichloroquinolin-8-yl | CH₃ | 121–124 |
| 167 | C₂H₅ | O | O | — | 5-chloroquinolin-8-yl | CH₃ | 152–157 |
| 168 | CH₃ | O | O | — | 5-chloro-7-bromo-quinolin-8-yl | CH₃ | 229–232 |
| 169 | CH₃ | O | S | — | pyrimidin-2-yl | CH₃ | |
| 170 | CH₃ | O | O | CH₂ | pyridaz-6-on-1-yl | CH₃ | |
| 171 | CH₃ | — | O | CH₂ | 4,5-dichloropyridaz-6-on-1-yl | CH₃ | |
| 172 | CH₃ | — | O | — | 1-methylpyridaz-6-on-3-yl | CH₃ | |
| 173 | CH₃ | O | O | — | 4-methyltetrahydropyran-2-yl | CH₃ | |
| 174 | (CH₃)₂N | — | O | — | 5-chloroquinolin-8-yl | CH₃ | |
| 175 | CH₃ | O | O | — | pyran-2-yl | CH₃ | |
| 176 | CH₃ | O | O | — | 2-methyl-pyran-6-on-4-yl | CH₃ | 162–165 |
| 177 | CH₃ | O | O | — | benzopyran-2-on-4-yl | CH₃ | 248–250 |
| 178 | CH₃ | O | O | CH₂ | benzo-1,4-dioxan-2-yl | CH₃ | 109–113 |
| 179 | CH₃ | O | O | CH₂ | 2,2-dimethyl-5-ethyl-1,3-dioxan-5-yl | CH₃ | |
| 180 | CH₃ | O | O | CH₂ | 2-methyl-1,3-dioxan-5-yl | CH₃ | |
| 181 | CH₃ | O | O | CH₂ | 1,2,3-thiadiazol-4-yl | CH₃ | 144–147 |
| 182 | CH₃ | O | O | CH₂ | 1,2,3-thiadiazol-5-yl | CH₃ | |
| 183 | CH₃ | O | O | CH₂ | fur-2-yl | CH₃ | |
| 184 | CH₃ | O | O | CH₂ | thien-2-yl | CH₃ | |
| 185 | CH₃ | O | S | CH₂ | fur-2-yl | CH₃ | 117–119 |
| 186 | CH₃ | O | O | CH₂ | 3-methylisoxazol-5-yl | CH₃ | 285–287 |
| 187 | CH₃ | O | O | CH₂ | thien-3-yl | CH₃ | |
| 188 | CH₃ | O | O | CH₂ | 2,3-dichlorothien-4-yl | CH₃ | 141–143 |
| 189 | CH₃ | — | O | — | 6-methylpyridin-3-yl | CH₃ | 116–120 |
| 190 | CH₃ | O | O | — | 6-methylpyridin-3-yl | C₂H₅ | |
| 191 | CH₃ | — | O | CH₂ | 1,2,3-thiadiazol-4-yl | CH₃ | 101–105 |
| 192 | CH₃ | — | O | — | quinolin-8-yl | CH₃ | 186–190 |
| 193 | CH₃ | O | S | — | benzoxazol-2-yl | CH₃ | 154–156 |
| 194 | CH₃ | O | O | CH₂ | pyrid-2-yl | CH₃ | |
| 195 | CH₃ | — | O | —CH₂CO— | 1-(2,3-dimethylhexamethyleneimine) | CH₃ | |
| 196 | CH₃ | O | O | CH₂ | 2-bromothien-4-yl | CH₃ | 130–133 |
| 197 | CH₃ | O | O | CH₂ | 2,5-dichlorothien-3-yl | CH₃ | 117–120 |
| 198 | CH₃ | O | O | —CH₂—CO— | 1-(2,3-dimethylhexamethyleneimine) | CH₃ | 1,5169 |
| 199 | CH₃ | O | O | —CH₂—CO— | 1-hexamethylene-imine | CH₃ | |
| 200 | CH₃ | O | O | —CH₂—CO— | piperidinyl | CH₃ | |
| 201 | (CH₃)₂N | — | O | —CH₂—CO— | 1-(2,3-dimethylhexamethyleneimine) | CH₃ | |
| 202 | CH₃ | O | S | — | benzothiazol-2-yl | CH₃ | 162–166 |
| 203 | CH₃ | O | O | — | 2-isopropyl-6-methylpyrimidin-4-yl | C₂H₅ | |
| 204 | CH₃ | O | O | — | 3,5,7-trichloroquinolin-8-yl | CH₃ | 207–210 |
| 205 | CH₃ | O | O | — | 3,7-dichloro-5-bromo-quinolin-8-yl | CH₃ | 248–250 |

The compounds of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparaion of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty aclohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of the compound of Example 1 is mixed with 10 parts by weight of N-methyl-alpha-pyrrolidone. A mixture is obtained which is suitable for application in the form of very fine drops.

II. 20 parts by weight of compound no. 5 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 19 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 178 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous disperson is obtained containing 0.02% by weight of the active ingredient.

V. 20 parts by weight of compound no. 111 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 89 is intimately mixed with 97 parts by weight of particulate kaolin. A dust is obtained containing 3% by weight of the active ingredient.

VII. 30 parts by weight of compound no. 196 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 185 is intimately mixed with 46 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year and the growth stage of the plants, and varies from 0.05 to 5 kg/ha, the higher rates being suitable for total elimination of vegetation.

The influence of representatives of compounds of the formula I on the growth of unwanted and crop plants is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate varied from ingredient to ingredient, and was either 1.0, 2.0 or 3.0 kg of active ingredient per hectare. After the agents had been applied, the vessels were lightly sprinkler-irrigated to induce germination and growth and to active the chemical agents. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or separately grown plants which were transplanted to the pots. No covers were placed on the pots in this treatment method. The application rate for postemergence treatment was 3.0 kg of active ingredient per hectare.

The pots were set up in the greenhouse-species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The test plants were Centaurea cyanus, Chenopodium album, Cyperus esculentus, Datura stramonium, Echinochloa crus-galli, Galium aparine, Gossypium hirsutum, Ipomoea spp., Lolium multiflorum, Mentha piperita, Nicandra physaloides, Oryza sativa, Sinapis alba, Solanum nigrum, Viola spp., and Zea mays.

In the experiments, for example compounds nos. 1, 20, 111, 143, 156, 161, 178, 186, 196 and 197, applied preemergence at 3.0 kg/ha, had a good herbicidal action.

On postemergence application, for instance compounds nos. 89, 111, 117, 119, 131, 185, 189, 191, 192, 193, 196, 198 and 202, applied at 3.0 kg/ha, combatted unwanted plants very successfully. For selective weed control, for example compounds nos. 5, 19 and 181 at 1.0 kg/ha, and compound no. 111 at 2.0 kg/ha, are suitable. Compounds nos. 39 and 177 at 0.5 kg/ha, and compounds nos. 176 and 185 at 1.0 kg/ha, combatted unwanted plants in rice and Indian corn with only slight damage, if any at all, to the crop plants.

In view of the good tolerance of the active ingredients and the numerous application methods possible, the compounds according to the invention may be used in a large number of crop plants other than those employed in the greenhouse experiments for removing unwanted plant growth.

The following crop may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |

-continued

| Botanical name | Common name |
|---|---|
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the compounds of the formula I may be mixed and applied together with numerous other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. To initiate the herbicidal action, spreader-stickers, non-phytotoxic oils and oil concentrates may also be added.

We claim:

1. A 1,2,4,6-thiatriazine, 1,1-dioxide ether of the formula

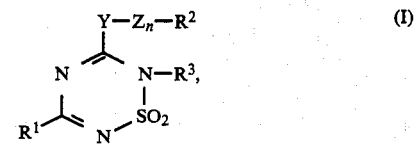

where $R^1$ is hydrogen, a saturated or unsaturated straight-chain or branched aliphatic radical of not more than 10 carbon atoms or a saturated, straight-chain or branched aliphatic radical of not more than 10 carbon atoms which is substituted by halogen, alkoxy or alkylmercapto of 1 to 4 carbon atoms, or is monoalkylamino or dialkylamino where alkyl is of 1 to 6 carbon atoms, cycloalkyl of 3 to 7 carbon atoms or a radical $R^4$—X—, where $R^4$ has the meanings given for $R^1$, with the exception of monoalkylamino and dialkylamino, and X is oxygen, sulfur, —SO— or —$SO_2$, $R^2$ is a 6-membered aromatic heterocyclic radical having 1 to 2 nitrogen atoms as ring members and is unsubstituted or substituted by alkyl of 1 to 4 carbon atoms, alkoxy of 1 to 4 carbon atoms, trifluoromethyl, cyano, nitro or halogen, or is a 5-membered aromatic heterocyclic radical which is unsubstituted or substituted by alkyl of 1 to 4 carbon atoms, alkoxy of 1 to 4 carbon atoms, trifluoromethyl, cyano, nitro or halogen and has 1, 2 or 3 heteroatoms selected from the group consisting of oxygen, sulfur or nitrogen, with the proviso that the rings have no more than one oxygen or one sulfur atom, or is a 5-membered or 6-membered benzofused aromatic heterocyclic radical which is unsubstituted or substituted by alkyl of 1 to 4 carbon atoms, alkoxy of 1 to 4 carbon atoms, trifluoromethyl, cyano, nitro or halogen and has 1,2 or 3 heteroatoms selected from the group consisting of oxygen, sulfur or nitrogen, with the proviso that the rings have no more than one oxygen or one sulfur atom and n is 0, $R^3$ is hydrogen, a saturated or unsaturated, straight-chain or branched aliphatic radical of not more than 10 carbon atoms which is substituted by halogen or alkoxy of 1 to 4 carbon atoms, or is cycloalkyl of 3 to 7 carbon atoms, Y is oxygen, sulfur, —SO—, or —$SO_2$—, Z is alkylene of 1 to 4 carbon atoms or —$(CH_2)_2$—O—$CH_2$—, —$(CH_2)_2O$— or —$CH_2$—CO—, and n is 0 or 1.

2. A 1,2,4,6-thiatriazine, 1,1-dioxide ether of the formula I as claimed in claim 1 in which $R^1$ is alkyl of 1 to 4 carbon atoms or a radical $R^4$—X—, where $R^4$ is alkyl of 1 to 4 carbon atoms and X is oxygen, $R^2$ is a free or benzofused pyridine radical which is unsubstituted or substituted by alkyl of 1 to 4 carbon atoms, nitro or halogen, $R^3$ is alkyl of 1 to 4 carbon atoms, Y is oxygen, Z is methylene and n is 0 or 1.

3. A 1,2,4,6-thiatriazine 1,1,-dioxide ether of the formula I as claimed in claim 1 in which $R^1$ is alkyl of 1 to 4 carbon atoms or a radical $R^4$—X—, where $R^4$ is alkyl of 1 to 4 carbon atoms and X is oxygen, $R^2$ is a free or benzofused pyrimidine, oxazole, thiazole, isoxazole, thiophene, furan, pyrrole, or 1,2,3-thiadiazole radical which may be substituted by alkyl or alkoxy, each of 1 to 4 carbon atoms, or by halogen, $R^3$ is alkyl of 1 to 4 carbon atoms, Y is oxygen or sulfur, Z is methylene and n is 0 or 1.

4. A 1,2,4,6-thiatriazine 1,1-dioxide ether of the formula I as claimed in claim 1 in which $R^1$ is a radical $R^4$—X—, where $R^4$ is methyl and X is oxygen, $R^2$ is pyridyl, methylpyridyl, nitropyridyl, quinolyl, 1,2,3-thiadiazolyl, furyl, 2-bromothienyl, 2,5-dichlorothienyl, 3-methylisoxazolyl, 2-isopropyl-6-methylpyrimidinyl, benzothiazol-2-yl or benzoxazol-2-yl, $R^3$ is methyl, Y is oxygen or sulfur, Z is methylene, dimethylene or —$CH_2$—CO—, $(CH_2)_2$—O— or —$(CH_2)_2$—O—$CH_2$ and n is 0 or 1.

5. A 1,2,4,6-thiatriazine 1,1-dioxide ether of the formula I as claimed in claim 1 in which $R^1$ is methoxy, $R^2$ is pyridyl which may be substituted by nitro, halogen or alkyl of 1 to 4 carbon atoms, $R^3$ is methyl, Y is oxygen and n is zero.

6. 6-Methyl-3-methoxy-(3-chloropyrid-5-yloxy)-6H-1,2,4,6-thiatriazine 1,1-dioxide.

7. A herbicide containing inert additives and a 1,2,4,6-thiatriazine 1,1-dioxide ether of the formula I as claimed in claim 1.

8. A process for combating the growth of unwanted plants wherein the plants and/or the soil are treated with a herbicidally effective amount of a 1,2,4,6-thiatriazine 1,1-dioxide ether of the formula I as claimed in claim 1.

* * * * *